United States Patent
Gordils Wallis

(10) Patent No.: US 6,332,775 B1
(45) Date of Patent: Dec. 25, 2001

(54) INSTRUMENT AND PROCESS FOR MINIMUM DISTANCE PLACEMENT IMPLANT—IMPLANT AND IMPLANT—NATURAL TOOTH AND MINIMUM PERIPHERAL PLACEMENT OF RESTORATION MATERIAL FOR CYLINDRICAL AND SCREWED IMPLANTS IN DENTISTRY

(76) Inventor: Antonio Jose Gordils Wallis, Av. Francisco de Miranda, Edif. Cavendes, Piso 12, Los Palos Grandes, 'Caracas-Venezuela, Apartado 68.606 Caracas 1062 (VE)

(*) Notice: Subject to any disclaimer, the term of this patent is extended or adjusted under 35 U.S.C. 154(b) by 0 days.

(21) Appl. No.: 09/643,405

(22) Filed: Aug. 22, 2000

(51) Int. Cl.[7] ................................................. A61C 19/04
(52) U.S. Cl. .............................................. 433/72; 433/75
(58) Field of Search .................................. 433/72, 74, 75, 433/76, 73; 33/513, 514

(56) References Cited

U.S. PATENT DOCUMENTS

| | | | |
|---|---|---|---|
| 2,910,773 | * 11/1959 | Walton | 433/72 |
| 3,344,525 | * 10/1967 | Harris | 433/75 |
| 4,251,210 | * 2/1981 | Weissman | 433/76 |
| 5,302,122 | * 4/1994 | Milne | 433/76 |
| 5,842,859 | * 12/1998 | Palacci | 433/72 |

OTHER PUBLICATIONS

Palacci, P., *Optimal Implant Positioning & Soft Tissue Manabement for the Branemark System*, Quintessescence Publishing Co., Inc., 1995, pp. 41–58.

* cited by examiner

Primary Examiner—John J. Wilson
Assistant Examiner—Melba Bumgarner
(74) Attorney, Agent, or Firm—Ladas & Parry

(57) ABSTRACT

An instrument for the placement of cylindrical or screwed dental implants has a lower portion and an upper portion having a diameter greater than a diameter of the lower portion with three horizontal extensions of respectively different lengths. In a lower third of the upper portion, an axial concavity is at an outer end of a longest of the extensions.

3 Claims, 2 Drawing Sheets

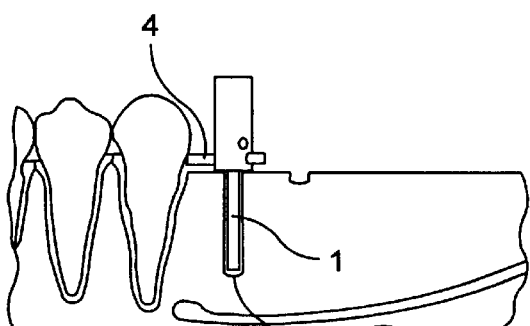
FIG. 5(III)

INSTRUMENT AND PROCESS FOR MINIMUM DISTANCE PLACEMENT IMPLANT— IMPLANT AND IMPLANT— NATURAL TOOTH AND MINIMUM PERIPHERAL PLACEMENT OF RESTORATION MATERIAL FOR CYLINDRICAL AND SCREWED IMPLANTS IN DENTISTRY

There is provided an instrument and process to locate a bone-integrating cylindrical or screwed type dental implant and restoration material.

When implant-implant and implant-natural tooth spacing is too close the restoration phase becomes extremely complicated because the space for the restoration material is insufficient and it is very difficult to achieve adequate inter-proximal niches for correct hygiene. On the contrary, when the distance between implant-implant and implant-natural tooth is too wide it will be necessary to prepare prosthetic structures with inadequate proximal projections, thereby impeding inter-proximal hygiene and creating the cantilever effect on the implants. The technique currently used for the placement of the implants in the maxillary arch superimposes a surgical splint that consists of a plastic reproduction of the teeth to be restored on the maxillary to indicated the position of the implants by means of perforations located in the coronal portion. Although this method is very reliable under certain circumstances, the perforations would be placed at a distance smaller than the minimum adequate distance.

SUMMARY OF THE INVENTION

With the instrument and process of this invention, the possibility of not achieving the minimum distance between implant-implant and implant-natural tooth would be reduced, thus increasing the probability of having a good case prognosis.

Such dental implants are small titanium cylinders that behave as artificial roots providing for retaining upper and lower total removable prosthesis, for placing total and partial fixed prosthesis, and for replacing unique tooth.

DETAILED DESCRIPTION OF INVENTION

Figure 1:
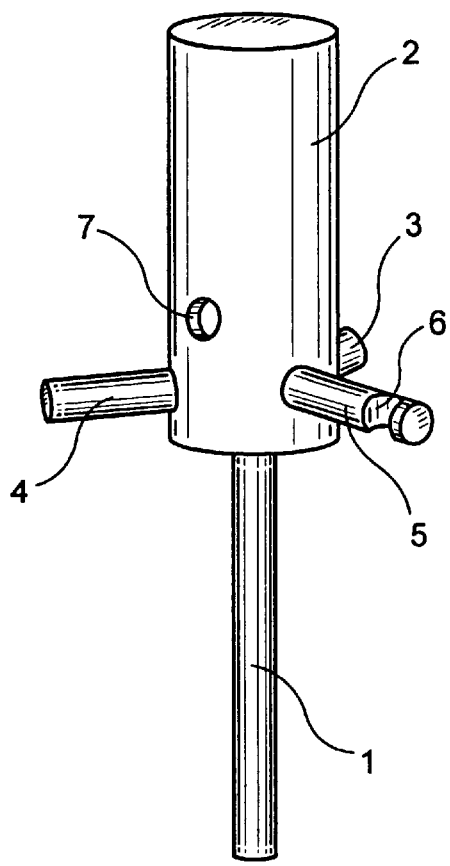
FIG. 1 Perspective view of the invention Instrument
Figure 2:
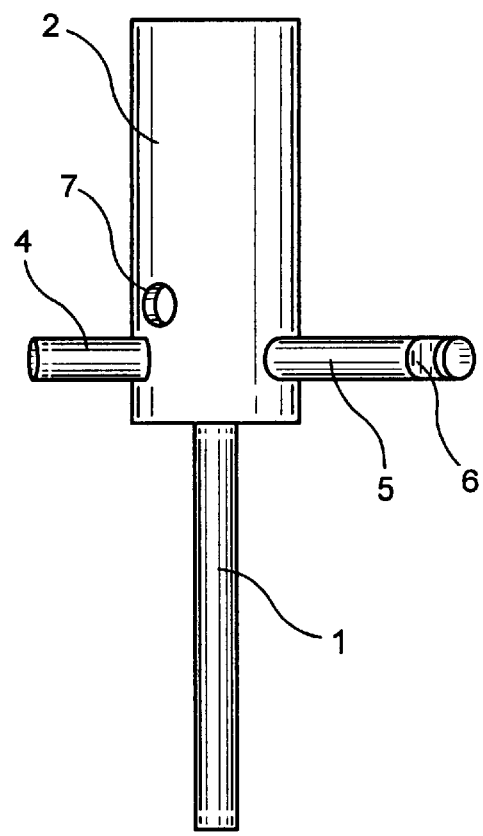
FIG. 2 Frontal view of the Instrument
Figure 3:
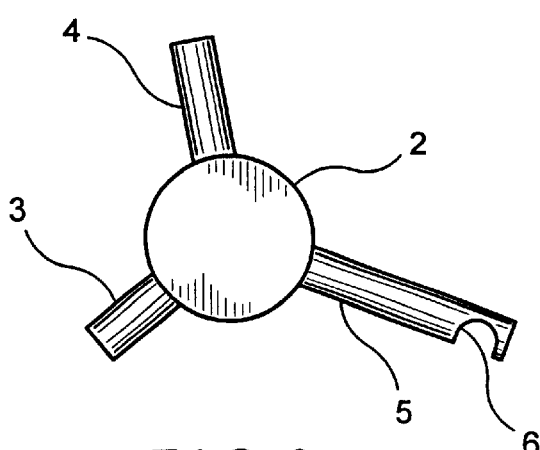
FIG. 3 Top plan view of the Instrument
Figure 4:
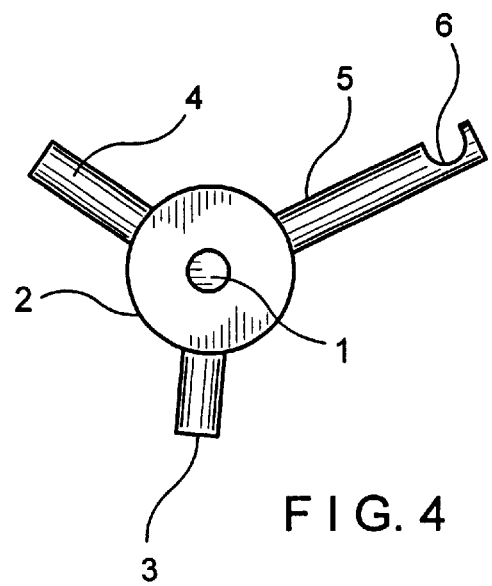
FIG. 4 View underneath the Instrument
Figure 5I:
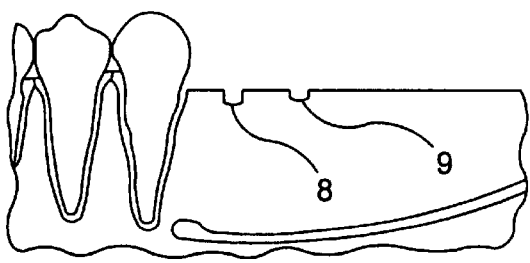
FIG. 5 Schematic sequence showing the steps of the procedure for which the Instrument was used.
Figure 5:
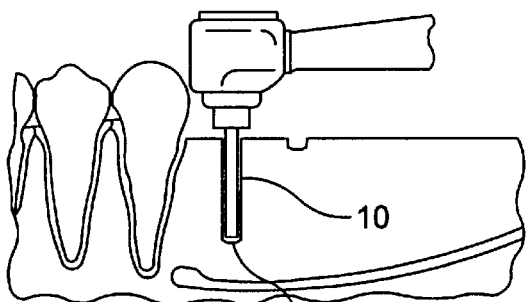
Figure 5:
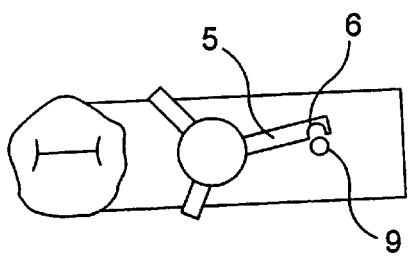
Figure 5V:
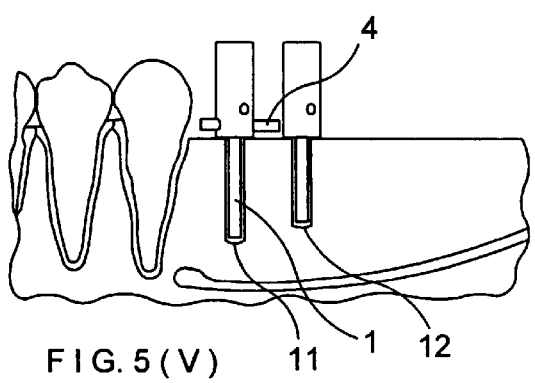
Figure 5:
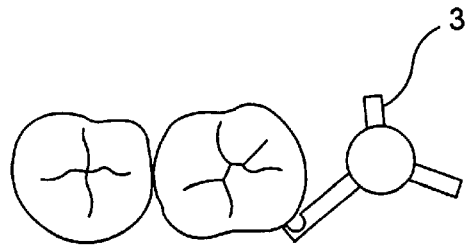

FIGS. 1, 2, 3 and 4 show the invention instrument. The instrument has one portion 1 that is lower in use on a lower maxillary arch or jawbone as shown in FIG. 5, and an axially opposite, upper portion 2 of greater diameter. Three transverse (i.e., horizontal in use as shown in FIG. 5) pins or extensions 3, 4 and 5 of respectively different lengths project from the lower third of the upper portion. An axial concavity 6 is at an outer end of a longest one of the extensions. The upper portion 2 also has a perforation or blind hole 7 in its lower third.

FIG. 5 shows the use of the invention.

FIG. 5 (I) shows the marks 8 and 9 made with the surgical splint.

FIG. 5 (II) shows the perforation (11) with the initial drill (10)

FIG. 5 (III) shows the lower portion 1 of the Instrument inserted into the perforation 11 and with extension 4 the distance between perforation 11 and the tooth is verified to assure the minimum distance required.

FIG. 5 (IV) shows the lower portion 1 of the Instrument inserted into perforation 11, and verified with the concavity 6 of extension 5, to confirm that the first perforation 11 and the second mark 9, have minimum separation.

FIG. 5 (V) shows the lower portion 1 of the Instrument inserted into perforation 11, and with extension 4, the distance between perforation 11 and 12 is verified to assure the minimum distance required.

FIG. 5 (VI) shows how the extension 3 is used as a visual guide for the minimum peripheral replacement of restoration material (not shown) and location of the buccal-lingual perforation.

What is claimed is:

1. An instrument for the placement of cylindrical or screwed dental implants, said instrument comprising:

a lower portion and an upper portion having a diameter greater than a diameter of the lower portion with three horizontal pin extensions respectively of longest, medium and shortest lengths in a lower third of the upper portion, an axial concavity being at an outer end of the longest pin extension.

2. Process for the placement of cylindrical or screwed implants with the instrument according to claim 1, wherein the lower portion is inserted in a first perforation and at least one of a minimum adequate distance to a second perforation is verified with the axial concavity by directing the longest pin extension toward the second perforation, a minimum adequate distance between the first perforation and a tooth is verified by directing the medium length pin extension towards the tooth, thereby verifying with an end of the medium length pin extension the minimum adequate distance between the first perforation and the tooth, an implant-implant minimum adequate distance is verified by directing the medium length pin extension towards a pin in the second perforation, thereby verifying with the end of the medium length pin extension the implant-implant minimum adequate distance, and a minimum peripheral location of restoration material is verified by directing an end of the shortest length pin extension toward the peripheral location, thereby locating the minimum peripheral location of the restoration material as well as a location of a buccal-lingual implant position.

3. The process according to claim 2, and further comprising locating the first and second perforations with a surgical splint.

* * * * *